(12) United States Patent
Bailon et al.

(10) Patent No.: US 7,049,415 B2
(45) Date of Patent: May 23, 2006

(54) PEGYLATED T20 POLYPEPTIDE

(75) Inventors: Pascal Sebastian Bailon, Florham Park, NJ (US); Chee-Youb Won, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/623,873

(22) Filed: Jul. 21, 2003

(65) Prior Publication Data

US 2004/0049018 A1    Mar. 11, 2004

Related U.S. Application Data

(60) Provisional application No. 60/398,195, filed on Jul. 24, 2002.

(51) Int. Cl.
*A61K 38/12*    (2006.01)
*C08H 1/00*     (2006.01)

(52) U.S. Cl. ........................... 530/402; 530/324
(58) Field of Classification Search ............... 530/402
See application file for complete search history.

(56) References Cited

U.S. PATENT DOCUMENTS

| | | | |
|---|---|---|---|
| 5,252,714 A | | 10/1993 | Harris et al. |
| 5,464,933 A | * | 11/1995 | Bolognesi et al. .......... 530/324 |
| 5,672,662 A | | 9/1997 | Harris et al. |
| 5,795,569 A | * | 8/1998 | Bartley et al. ............. 424/85.1 |
| 5,955,422 A | | 9/1999 | Lin |
| 5,959,265 A | | 9/1999 | Van Ligten |
| 5,990,237 A | | 11/1999 | Bentley et al. |
| 6,015,881 A | | 1/2000 | Kang et al. |
| 6,340,742 B1 | | 1/2002 | Burg et al. |
| 2003/0153694 A1 | | 8/2003 | Rosen et al. |

FOREIGN PATENT DOCUMENTS

| | | |
|---|---|---|
| WO | WO 94 28920 A1 | 12/1994 |
| WO | WO 99 48513 A1 | 9/1999 |
| WO | WO 00/24697 | 5/2000 |
| WO | WO 01 02017 A2 | 1/2001 |
| WO | WO 01 02017 A3 | 1/2001 |

OTHER PUBLICATIONS

Reddy, K. R., Controlled-Release, Pegylation, Liposomal Formulations: New Mechanisms in the Delivery of Injectable Drugs (2000), The Annals of Pharmacotherapy, vol. 34, pp. 915-923.*
Bailon, Pascal, et al., Bioconjugate Chemistry, vol. 12, No. 2, pp. 195-202 (2001).
Yowell, S. L., et al., Cancer Treatment Reviews, vol. 28, Supplement A, pp. 3-6 (2002).
Topchiyeva, I.N., et al., Polymer Science USSR, XP000261916, vol. 32, No. 5, pp. 833-851 (1990).
Chem. Soc. vol. 85, p. 2149 (1963).
Sheppard, R.C. et. al., J. Chem. Soc. Chem. Comm., 165-166, (1985).

* cited by examiner

*Primary Examiner*—Bruce R. Campell
*Assistant Examiner*—Thomas S. Heard
(74) *Attorney, Agent, or Firm*—George W. Johnston; Dennis P. Tramaloni; Samuel H. Megerditchian

(57) ABSTRACT

Pegylated T20 polypeptide compounds are provided. Also provided are pharmaceutical compositions containing pegylated T20 polypeptide compounds, and methods of making and using such compounds and compositions.

95 Claims, No Drawings

SEQUENCE LISTING

```
<160> NUMBER OF SEQ ID NOS: 1

<210> SEQ ID NO 1
<211> LENGTH: 36
<212> TYPE: PRT
<213> ORGANISM: Artificial
<220> FEATURE:
<223> OTHER INFORMATION: Peptide sequence was synthetically derived.
<220> FEATURE:
<221> NAME/KEY: MOD_RES
<222> LOCATION: (36)..(36)
<223> OTHER INFORMATION: Residue No. 36 is optionally modified with an
      amino group.

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30
```

-continued

```
Trp Asn Trp Phe
              35
```

PEGYLATED T20 POLYPEPTIDE

This application claims the benefit of the U.S. Provisional Application 60/398,195, filed on Jul. 24, 2002.

FIELD OF THE INVENTION

The present invention relates to pegylated T20 polypeptide compounds, and to related methods of using and making such compounds, such as in pharmaceutical compositions and therapeutic methods of treatment.

BACKGROUND OF THE INVENTION

Some viruses, especially HIV, must undergo a complex process called fusion in order to enter the host cell and reproduce. During fusion, the outer membrane of the virus fuses with the membrane of the host cell. In the case of HIV, the outer membrane of the HIV virus fuses with the membrane of the CD4+ T cell during reproduction.

T20 is a member of a new class of antiviral agents that inhibit virus/membrane fusion. In the case of HIV, this provides two salutary effects: the reproduction of HIV is blocked and resultant death of the CD4+ T cells does not occur.

Data from two large, internationally conducted Phase III trials indicate that combination therapy with T-20 reduced HIV to undetectable levels in the blood in at least twice the percentage of patients and provided an improved immune response at 24 weeks, as compared to those who took combination therapy without T-20. Additionally, those receiving T-20 were less likely to experience virological failure or relapse over 24 weeks.

In the first Phase III trial, conducted in North America and Brazil, 37 percent of patients who were treated with T-20 in combination with an optimized background regimen had undetectable blood levels (less than 400 copies/mL) of HIV at 24 weeks, compared to 16 percent who received an optimized background regimen alone (p<0.0001). Combination therapy with T-20 further reduced HIV viral load to less than 50 copies/mL in 20 percent of patients as compared to 7 percent who took combination therapy alone (P=0.0002).

The primary efficacy endpoint for the study, the mean difference in the magnitude of decrease in HIV between the two groups in the study, was 0.934 log 10 copies/mL (p<0.0001). Patients who received T-20 as part of their combination regimen achieved a reduction in HIV levels of 1.697 1 log10 copies/mL, compared to 0.763 log 10 copies/mL for those in the control arm. Furthermore, 52 percent of patients receiving T-20 experienced a 1.0 log10 or greater reduction in HIV levels, compared to 29 percent who did not receive T-20 (P<0.0001). Patients in the T-20 arm experienced a mean CD4+ cell increase of 76 cells/mm3, as compared to 32 cells/mm3 in the control arm (p<0.0001).

Results from the second Phase III clinical trial, conducted in Europe and Australia, were consistent with findings from the first study. 28 percent of patients who were treated with T-20 in combination with an optimized background regimen had undetectable blood levels (less than 400 copies/mL) of HIV at 24 weeks, compared to 14 percent receiving an optimized background regimen alone (p<0.0001). Combination therapy with T-20 further reduced HIV viral load to less than 50 copies/mL in 12 percent of patients as compared to 5 percent who took combination therapy alone (P=0.0099).

The mean difference in the magnitude of decrease in HIV between the two arms at 24 weeks was 0.78 log 10 copies/mL (p<0.0001). Patients who received T-20 as part of their combination regimen achieved a mean reduction in HIV levels of 1.43 log 10 copies/mL, compared to a mean of 0.65 log 10 copies/mL for those in control arm. Furthermore, 43 percent of patients receiving T-20 experienced a 1.0 log 10 or greater reduction in HIV levels, compared to 21 percent who did not receive T-20 (P<0.0001). Patients in the T-20 arm experienced a mean CD4+ cell increase of 65 cells/mm3, as compared to 38 cells/mm3 in the control arm (p=0.023).

At entry, an optimized background regimen (consisting of three to five drugs, including up to two newly approved or investigational drugs, if appropriate) was chosen for each patient based on treatment history and antiretroviral resistance testing. After selection of the regimen, patients were randomized 2:1 to receive either the regimen in combination with T-20 or the regimen alone. Patients randomized to T-20 received T-20 administered as one 90 mg subcutaneous self-injection twice-daily.

Viral resistance to currently approved anti-HIV drugs is a significant issue in the clinical management of HIV today. Many patients who begin combination antiretroviral treatment with currently approved medications will develop resistance to one or more of these agents over time. Research suggests, however, that T20 may be unaffected by resistance to any of the currently approved antiretroviral classes. (Data presented at the 5th International Workshop on Drug Resistance and Treatment Strategies in Scottsdale, Ariz., Jun. 4–8, 2001). Additional experiments show that the in vitro activity of T20 is not affected by mutations associated with resistance to reverse transcriptase inhibitors and protease inhibitors.

Like many polypeptide therapeutic agents, T20 is generally administered by injection. Current therapeutic protocols often involve more than one daily injection.

It would, therefore, be advantageous to provide T20 polypeptides and pharmaceutical compositions having improved performance and pharmacokinetic characteristics. It would be particularly advantageous to provide for lower therapeutic doses of T20, less frequent administrations, and/or extended duration of action.

These and other objects of the present invention are described in greater detail below.

SUMMARY OF THE INVENTION

The present invention provides a compound of formula:

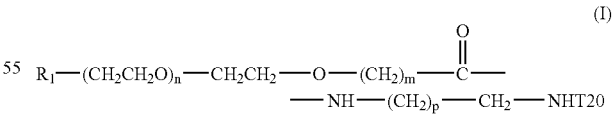

wherein
$R_1$ is a capping group,
m is from 1 to 17,
n is from 10 to 1,000,
p is from 1 to 3, and
NHT20 is a T20 polypeptide covalently bonded through its terminal α-amino group.

In one embodiment of the compound of the present invention $R_1$ is methoxy, m is 1, n is from 100 to 750, and p is 3.

Also provided is a pharmaceutical composition comprising, in admixture with a pharmaceutically acceptable excipient, a compound of formula (I), wherein $R_1$, m, n, p, and NHT20 are defined as above.

In one embodiment of the pharmaceutical composition of the present invention $R_1$ is methoxy, m is 1, n is from 100 to 750, and p is 3.

The present invention further provides a method of inhibiting HIV infection comprising administering a pharmaceutical composition comprising, in admixture with a pharmaceutically acceptable excipient, a compound of formula (I), wherein $R_1$, m, n, p, and NHT20 are defined as above.

In one embodiment of the method of inhibiting HIV infection $R_1$ is methoxy, m is 1, n is from 100 to 750, and p is 3.

Further provided is a method for making a pegylated T20 polypeptide comprising reacting a T20 polypeptide with a polyethylene glycol aldehyde of formula:

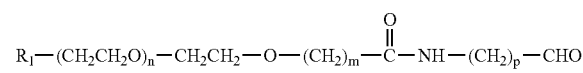
(II)

wherein $R_1$, m, n, n, and p are defined as above to produce a compound of formula (I):

wherein the polyethylene glycol aldehyde molecule is bonded to the N-terminal amino group of the T20 polypeptide.

Also provided by the invention is a compound of formula:

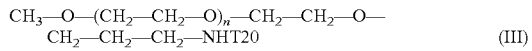
(III)

wherein n is from 10 to 1,000 and NHT20 is a T20 polypeptide covalently bonded through its terminal α-amino group.

Also provided by the invention is a pharmaceutical composition comprising, in admixture with a pharmaceutically acceptable excipient, a compound of formula (III), wherein n is from 10 to 1,000 and NHT20 is a T20 polypeptide covalently bonded through its terminal α-amino group.

Also provided is a method of inhibiting HIV infection comprising administering a pharmaceutical composition comprising, in admixture with a pharmaceutically acceptable excipient, a compound of formula (III), wherein n is from 10 to 1,000 and NHT20 is a T20 polypeptide covalently bonded through its terminal α-amino group.

DETAILED DESCRIPTION OF THE INVENTION

As noted above, T20 is a "fusion inhibitor" polypeptide. T20 consists of 36 amino acids. The polypeptide sequence of T20 is:

YTSLIHSLIEESQNQQEKNEQELLELDK-
WASLWNWF [SEQ.ID.NO:1]

The N-terminus (or amino terminus) amino acid is tyrosine (Y). The C-terminus (or carboxy terminus) amino acid is phenylalanine (F).

As described in FIG. 1 of U.S. Pat. No. 5,464,933 (SEQ ID:1), which is hereby incorporated by reference in its entirety, the T20 polypeptide sequence may be blocked/derivatized at one or both of its amino and carboxy termini. As described in U.S. Pat. No. 5,464,933, the tyrosine amino terminus may be blocked/derivatized with an acyl group and the phenylalanine carboxy-terminus may be blocked/derivatized with an amino group (the latter resulting in a conversion of the —COOH→—CONH$_2$).

As used herein, "T20" shall be understood to mean [SEQ.ID.NO:1], optionally blocked at the phenylalanine C-terminus with an amino group. In other words, when reference is made to "T20," the phenylalanine C-terminus is either —COOH or CONH$_2$.

The present invention provides pegylated T20 compounds of the following formula:

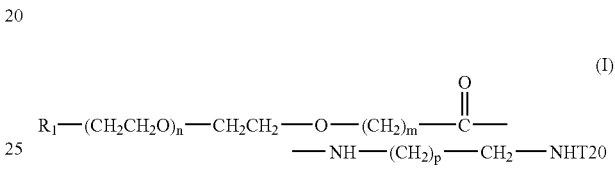
(I)

wherein
$R_1$ is a capping group,
m is from 1 to 17,
n is from 10 to 1,000,
p is from 1 to 3, and
NHT20 is a T20 polypeptide covalently bonded through its terminal α-amino group.

As used herein the $R_1$ "capping group" is any suitable chemical group which, depending upon preference, is generally unreactive or generally reactive with other chemical moieties. In the above compound the polyethylene glycol is covalently bonded to the α-amino group of T20. The $R_1$ capping group is selected to permit or prevent bifunctionality, e.g., covalent attachment to a second chemical moiety of interest.

In the case that the capping group is generally unreactive with other chemical moieties, $R_1$ is relatively inert and therefore will not covalently bond with another chemical moiety. Suitable generally unreactive $R_1$ capping groups include: hydrogen, hydroxyl, lower alkyl, lower alkoxy, lower cycloalkyl, lower alkenyl, lower cycloalkenyl, aryl, and heteroaryl.

As used herein, the term "lower alkyl", means a substituted or unsubstituted, straight-chain or branched-chain alkyl group containing from 1 to 7, preferably from 1 to 4, carbon atoms, such as methyl, ethyl, n-propyl, isopropyl, n-butyl, sec.butyl, tert.butyl, n-pentyl, n-hexyl, n-heptyl and the like. The lower alkyl is optionally substituted with one or more groups independently selected from halogen, lower alkyl, lower alkoxy, lower cycloalkyl, lower alkenyl, lower cycloalkenyl, aryl, and heteroaryl.

The term "lower alkoxy" means a lower alkyl group as defined earlier which is bonded via an oxygen atom, with examples of lower alkoxy groups being methoxy, ethoxy, n-propoxy, isopropoxy, n-butoxy, sec.butoxy, tert.butoxy, n-pentoxy and the like. The lower alkoxy is optionally substituted with one or more groups independently selected from halogen, lower alkyl, lower alkoxy, lower cycloalkyl, lower alkenyl, lower cycloalkenyl, aryl, and heteroaryl.

The term "lower cycloalkyl" means a cycloalkyl group containing from 3 to 7, preferably from 4 to 6, carbon atoms, i.e. cyclopropyl, cyclobutyl, cyclopentyl, cyclohexyl or cycloheptyl. The lower cycloalkyl is optionally substituted with one or more groups independently selected from halogen, lower alkyl, lower alkoxy, lower cycloalkyl, lower alkenyl, lower cycloalkenyl, aryl, and heteroaryl.

As used herein, the term "lower alkenyl" means a straight-chain or branched-chain alkenyl group containing from 2 to 7, preferably from 2 to 5, carbon atoms, e.g., ethenyl, butenyl, pentenyl, hexenyl and the like. The lower alkenyl is optionally substituted with one or more groups independently selected from halogen, lower alkyl, lower alkoxy, lower cycloalkyl, lower alkenyl, lower cycloalkenyl, aryl, and heteroaryl.

The term "lower cycloalkenyl" means a substituted or unsubstituted, cycloalkenyl group containing from 4 to 7 carbon atoms, e.g., cyclobutenyl, cyclopentenyl, cyclohexenyl and the like. The lower cycloalkenyl is optionally substituted with one or more groups independently selected from halogen, lower alkyl, lower alkoxy, lower cycloalkyl, lower alkenyl, lower cycloalkenyl, aryl, and heteroaryl.

The term "aryl" means a phenyl or naphthyl group which is unsubstituted or optionally mono- or multiply-substituted by halogen, lower alkyl, lower alkoxy, trifluoromethyl, hydroxyl, carboxylic acid, carboxylic ester, nitro, amino, or phenyl, particularly by halogen, lower alkyl, lower alkoxy, trifluoromethyl, hydroxyl, nitro, amino and phenyl.

The term "heteroaryl" means a 5- or 6-membered heteroaromatic group which contains one or more hetero atoms selected from N, S, and O and which may be benz-fused and/or substituted in the same manner as "aryl" defined earlier.

Preferred generally unreactive $R_1$ capping groups include methoxy, hydroxyl, or benzyloxy. An especially preferred, $R_1$ capping group is methoxy. When $R_1$ is methoxy the pegylated polypeptide compounds are sometimes referred to herein, in part, as "mPEG" compounds, wherein the "m" stands for methoxy.

If the $R_1$ capping group is generally reactive with other chemical moieties, then $R_1$ is a functional group capable of reacting with some functional group, such as an amine and/or sulfhydryl in a peptide and/or protein. In such a case, $R_1$ may be a functional group that is capable of reacting readily with electrophilic or nucleophilic groups on other molecules, in contrast to those groups that require strong catalysts or highly impractical reaction conditions in order to react. If $R_1$ is relatively reactive, the polyethylene glycol aldehyde may covalently bond with another chemical moiety.

Examples of suitable generally reactive $R_1$ capping groups include: halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

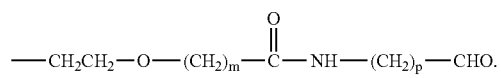

The term "halogen" means fluorine, chlorine, bromine, or iodine. A preferred generally reactive $R_1$ capping group is

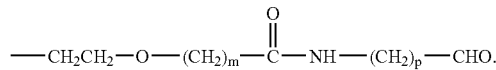

When this $R_1$ capping group is present, it will be appreciated that in the compounds of the present invention the first m, n, and/or p may be the same or different from the second m, n, and/or p in the formula. It is preferred, however, that both m's have the same value, both n's have the same value, and both the p's have the same value.

In the present invention, m is from 1 to 17. In a preferred embodiment, m is from 1 to 14. More preferably m is from 1 to 7, and even more preferably, m is from 1 to 4. Most preferably, m is 1.

In the present invention, n is from 10 to 1,000. In a preferred embodiment of the present invention n is from 20 to 1,000. Preferably, n is from 50 to 1,000, even more preferably n is from 75 to 1,000. Most preferably, n is from 100 to 750.

In the present invention, p is from 1 to 3. Preferably, p is 3.

In preferred embodiments, p is 3, $R_1$ is methoxy, m is 1, and n is from 100 to 750; or p is 2, $R_1$ is methoxy, m is 1, and n is from 100 to 750; or p is 1, $R_1$ is methoxy, m is 1, and n is from 100 to 750.

The present invention provides embodiments of formula (I),
  wherein $R_1$ is methoxy, m is 1, n is from 100 to 750, p is 3, and NHT20 is a T20 polypeptide covalently bonded through its terminal α-amino group.

As noted above, the pegylated T20 compounds of the invention covalently link the α-amino group of T20 to a polyethylene glycol derivative having a particular structure. The pegylated compounds may be made in any manner desired, but generally they are prepared by reacting T20 with separately prepared polyethylene glycol derivatives. For example, the T20 polypeptide may be pegylated by blocking all lysine residues and reacting this blocked T20 with a polyethylene glycol derivative. The blocked lysine residues of the T20 polypeptide are then deblocked, resulting in a terminally pegylated T20.

The T20 polypeptide may be prepared in any suitable manner. For example, the compounds may be synthesized using the classic Merrifield solid phase synthesis techniques involving a solid phase method employing Boc-amino acid (Chem. Soc., 85, 2149, 1963), by using manual or automated procedures, using a solid phase method employing an Fmoc-amino acid (Sheppard, R. C. et al., J.Chem. Soc. Chem. Comm., pp. 165–166 (1985)), using an Advanced Chemtech model 200 available from Advanced Chemtech., Louisville, Ky., using a Millipore 9050+ available from Millipore, Bedford Mass., or other available instrumentation.

T20 may be produced by incorporating cDNA coding compounds of the invention into functional viral or circular plasmid DNA vectors. The vectors or plasmids can be used to transfect or transform selected microorganisms.

The transformed or transfected microorganisms can be cultured under conditions that are conducive to express vector-borne DNA sequences and isolation of the desired peptides from the growth medium can be achieved. (See, for example U.S. Pat. No. 5,955,422, the entirety of which is incorporated herein by reference as if recited in full.)

T20 may also be prepared by standard recombinant DNA technology using techniques that are well known in the art.

For example, the procedures outlined in Sambrook et al. *Molecular Cloning: A Laboratory Manual*, 2nd edition, (Cold Spring Harbor Press, Cold Spring Harbor, N.Y.) or Ausubel et al., *Current Protocols in Molecular Biology*, John Wiley and Sons, New York (1995), both of which are herein incorporated by reference.

A particular method for making T20 is described in U.S. Pat. No. 6,015,881 which is hereby incorporated.

After cleavage and deprotection, T20 may be purified by any suitable means. For example, ion exchange, gel filtration chromatography and/or a reverse-phase column/HPLC system can be used to purify full length T20 from fragments thereof. In the case when a T20 precursor is first prepared, with a blocking/protecting group attached to the N-terminus (e.g., acyl group) and/or the C-terminus (e.g., amino group), one or both of those groups may be removed using known techniques.

The amino acid sequence of T20 may be confirmed and identified using standard amino acid analysis as well as manual and automated Edman degradation and determination of each amino acid. HPLC analysis and mass spectrometry may also be used to verify the production of T20.

Polyethylene glycol aldehyde compounds which may be reacted with T20 may be made in any desired manner. It is preferred, however, that the polyethylene glycol be made in accordance with the methods described in U.S. patent application Ser. No. 60/398,196, filed Jul. 24, 2002, entitled "Polyethylene Glycol Aldehydes," the entirety of which is hereby incorporated by reference.

Generally, a polyethylene glycol aldehyde of the formula:

$$R_1-(CH_2CH_2O)_n-CH_2CH_2-O-(CH_2)_m-\overset{O}{\underset{\|}{C}}-NH-(CH_2)_p-CHO \qquad (II)$$

wherein $R_1$ m, n, and p are defined as above is used to pegylate the T20. The polyethylene glycol aldehyde used to pegylated the T20 may be prepared by any suitable means. One preferred polyethylene glycol aldehyde is prepared as follows:

Polyethylene glycol aldehydes of varying size (e.g., varying n values) may be prepared by following the general reaction scheme above.

The pegylated T20 compounds of the present invention may be prepared by any suitable means. Further provided by the invention, however, is a method for pegylating a T20 polypeptide comprising reacting a T20 polypeptide, NHT20, with a polyethylene glycol aldehyde of formula:

$$R_1-(CH_2CH_2O)_n-CH_2CH_2-O-(CH_2)_m-\overset{O}{\underset{\|}{C}}-NH-(CH_2)_p-CHO \qquad (II)$$

wherein $R_1$, m, n, n, and p are defined as above;
to produce a compound of formula:

$$R_1-(CH_2CH_2O)_n-CH_2CH_2-O-(CH_2)_m-CO-NH-(CH_2)_p-CH_2-NHT20 \qquad (I)$$

wherein the polyethylene glycol aldehyde molecule is bonded to the N-terminal amino group of the T20 polypeptide.

The pegylated T20 is prepared by adding T20 and the PEG reagent in a molar ratio range of 1:1 to 1:100. The T20 has a free α-amino group (any acyl group is removed) and either a free carboxy group or an amino-protected carboxy group, as discussed above. The reaction mixture is placed in a borate, phosphate, or tri buffer at room temperature or 4 degrees Celsius for about 0.5 to 24 hours at a pH range of 5.5 to 7.4. The molar ratio of PEG reagent to peptide/proteins is between 1:1 to 100:1. The concentration of peptide/proteins is between 1 to 10 mg/ml. The concentration of buffer is usually 10 to 500 mM.

The pegylated T20 is purified by taking the reaction mixture of pegylated T20 and diluting it with an equilibration buffer (20 mM Tris, pH 7.5). The resulting mixture is then applied on a Q-Sepharose column. After the mixture is applied on the QA column, it is washed with the equilibration buffer eluted with 75 M NaCl; eluted with 200 mM NaCl; eluted with 1M NaCl; and regenerated with 1M HOAC+1M NaCl and 0.5 NaOH.

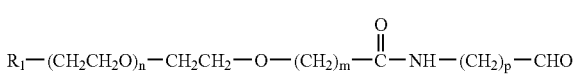

Reaction Scheme for mPEG$_{10k}$-butanoaldehyde (1) H$_3$C-O-(CH$_2$CH$_2$O)$_n$-CH$_2$CH$_2$CH$_2$-OH $\xrightarrow{\text{Potassium t-butoxide}}_{\text{t-Butyl bromoacetate}}$ (2) H$_3$C-O-(CH$_2$CH$_2$O)$_n$-O-CH$_2$-C(=O)-O-(CH$_3$)$_3$ $\xrightarrow{\text{Hydrolysis}}$ (3) H$_3$C-O-(CH$_2$CH$_2$O)$_n$-O-CH$_2$-C(=O)-OH $\xrightarrow[\text{1-hydroxybenzotriazole/}]{\text{4-aminobutyraldehyde diethyl acetal}}_{\text{dicyclohexylcarbodiimide}}$ (4) H$_3$C-O-(CH$_2$CH$_2$O)$_n$-O-CH$_2$-C(=O)-NH-(CH$_2$)$_3$-CH(OCH$_2$CH$_3$)$_2$ $\xrightarrow{10\% \text{ CF}_3\text{COOH}}$ (5) H$_3$C-O-(CH$_2$CH$_2$O)$_n$-O-CH$_2$-C(=O)-NH-(CH$_2$)$_3$-CHO By using reverse phase HPLC, a it is possible to readily separate and isolate the N-terminal, monopegylated product from other byproducts in the mixture.

In preferred embodiments of the pegylated T20 polypeptides of the present invention, p is 3, $R_1$ is methyl, m is 1, and n is from 100 to 750; or p is 2, $R_1$ is methoxy, m is 1, and n is from 100 to 750; or p is 1, $R_1$ is methoxy, m is 1, and n is from 100 to 750.

The present invention also provides a pegylated T20 polypeptide of the following formula:

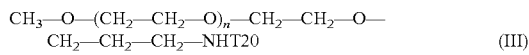
CH$_2$—CH$_2$—CH$_2$—NHT20 (III)

wherein n is from 10 to 1,000 and NHT20 is a T20 polypeptide covalently bonded through its terminal α-amino group. In one embodiment n is approximately 225, for example 227.

This pegylated T20 polypeptide may be made in any desired manner, preferably, it is made by the method described in Example 3.

The pharmaceutical compositions of the invention comprise, in admixture with a pharmaceutically acceptable excipient, a compound of formula (I), wherein $R_1$, m, n, p, and NHT20 are defined as above.

The pharmaceutical compositions of the present invention comprising pegylated T20 polypeptides or the salts thereof, may be manufactured in any desired manner, e.g., by means of conventional mixing, encapsulating, dissolving, granulating, emulsifying, entrapping, or lyophilizing processes. These pharmaceutical preparations may be formulated with therapeutically inert, inorganic or organic excipients and carriers. Suitable excipients for injection include water, alcohols, polyols, glycerine, vegetable oils, phospholipids and surfactants.

The pharmaceutical preparations may also contain preserving agents, solubilizing agents, stabilizing agents, wetting agents, emulsifying agents, sweetening agents, coloring agents, flavoring agents, salts for varying the osmotic pressure, buffers, coating agents, or antioxidants. They may also contain other therapeutically valuable substances, including additional active ingredients.

The formulations suitable for parenteral (including subcutaneous, intramuscular, intravenous, intradermal, intratracheal, and epidural) administration may conveniently be presented in unit dosage form and may be prepared by conventional pharmaceutical techniques. Such techniques include the step of bringing into association the pegylated T20 polypeptides and the pharmaceutical carrier(s) or excipient(s). In general, the formulations are prepared by uniformly and intimately bringing into association the pegylated T20 polypeptides with liquid carriers. Formulations suitable for parenteral administration include: aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) conditions requiring only the addition of the sterile liquid carrier, for example, water for injections, immediately prior to use.

Preferred unit dosage formulations are those containing a daily dose or unit, daily sub-dose, as herein above recited, or an appropriate fraction thereof, of the administered ingredient.

Preferably, the pegylated T20 polypeptide is in unit dosage form. As used herein, "unit dosage form," means that an amount appropriate for a single dose the pegylated T20 polypeptide is in a premeasured and/or prepackaged form. This allows for convenient preparation of the pegylated T20 polypeptide for administration, and may even allow for self-administration by the patient. The unit dosage amount will obviously depend on the amount of pegylated T20 polypeptide to be delivered, and the frequency of dosing.

The pegylated T20 polypeptide may also be provided in a lyophilized powder form in a unit dosage amount, suitable for reconstitution with a pharmaceutically acceptable excipient just prior to the time of administration.

A particular pharmaceutical composition of the invention comprises, in admixture with a pharmaceutically acceptable excipient, a compound of formula (I), wherein $R_1$ is methoxy, m is 1, n is from 100 to 750, and p is 3.

Another pharmaceutical composition of the invention is a pharmaceutical composition comprising, in admixture with a pharmaceutically acceptable excipient, a compound of formula (III), wherein n is from 10 to 1,000 and NHT20 is a T20 polypeptide covalently bonded through its terminal α-amino group. In one embodiment n is approximately 225, for example 227.

The present invention further provides methods of inhibiting HIV infection comprising administering to a patient a pharmaceutical composition comprising, in admixture with a pharmaceutically acceptable excipient, a compound of formula (I), wherein $R_1$, m, n, p, and NHT20 are defined as above.

The pegylated T20 polypeptides are generally administered in the manner (unpegylated) T20 polypeptides are presently administered. Modifications may be made, however, to take advantage of the improved pharmacokinetic properties of the pegylated T20 polypeptides.

In the method of inhibiting HIV of the invention, the pharmaceutical composition may be administered in any suitable manner and route. In a preferred method the pegylated T20 polypeptide is administered in the form of an injectable solution or suspension. Preferably, the injectable solution or suspension is administered by subcutaneous injection or intravenously.

In another preferred method, the pegylated T20 polypeptide is administered though a transdermal delivery device, e.g., a transdermal patch.

In the method of inhibiting HIV of the invention, the pharmaceutical composition may be administered in any suitable dosage and schedule. The pharmaceutical compositions of the invention can be administered in any form, and via any route, desired. Generally, however, the pegylated T20 polypeptides of the present invention are administered parenterally, for example, in the form of injection solutions.

Determination of a therapeutically effective amount is within the skill in the art, and the therapeutically effective amount or dosage of a pegylated T20 polypeptide according to this invention may vary and will be adjusted to the individual requirements in each particular case. In general, in the case of parenteral administration to adult humans weighing approximately 70 Kg, a daily dosage of about 5 mg to about 300 mg, preferably from about 50 mg to about 200 mg, should be appropriate, although the upper limit may be exceeded when indicated. The dosage may be administered as a single dose, in divided doses, or as continuous infusion. Daily and, more preferably, weekly administrations may be employed.

The present invention also provides a method of inhibiting HIV infection comprising administering a pharmaceutical composition comprising, in admixture with a pharmaceutically acceptable excipient, a compound of formula (I), wherein $R_1$ is methoxy, m is 1, n is from 100 to 750, and p is 3.

Also contemplated within the scope of the invention is a method of inhibiting HIV infection comprising administering a pharmaceutical composition comprising, in admixture with a pharmaceutically acceptable excipient, a compound of formula (III), wherein n is from 10 to 1,000 and NHT20 is a T20 polypeptide covalently bonded through its terminal α-amino group. In one embodiment n is approximately 225, for example 227.

The following examples are provided to further illustrate the compounds, compositions, and methods of the present invention. These examples are illustrative only and are not intended to limit the scope of the invention in any way.

EXAMPLE 1

Preparation of $PEG_{10K}$-butanoaldehyde mPEG of molecular weight 10,000 (30.0 g, 3 mmol) in 240 mL of toluene was azeotropically dried by refluxing for 2 hours, followed by the removal of 120 mL of toluene. The resulting solution was cooled to room temperature then potassium tert-butoxide (0.68 g, 6 mmol) in 20 ml of absolute tert-butanol and 20 ml of toluene was added to the PEG solution. The resulting mixture was stirred for two hours at room temperature under argon. Tert-butyl bromoacetate (1.00 mL, 6.75 mmol) was added to the reaction via syringe and the reaction was stirred overnight at room temperature under argon. The reaction solution was then condensed by rotary evaporation. The residue was precipitated by addition to diethyl ether. The precipitated $mPEG_{10k}$ t-butyl carboxymethyl ester product was filtered off and dried in vacuo. Yield: 28 g. NMR ($d_6$-DMSO): 1.40 ppm (t, 9H, —$CH_3$); 3.21 ppm (s, —$OCH_3$); 3.50 ppm (s, —O—$CH_2CH_2$—O—); 3.96 ppm (s, 2H, —O—$CH_2$—COO—).

$mPEG_{10k}$ t-butyl carboxymethyl ester (26.5 g) was then dissolved in 350 mL of 1N sodium hydroxide and the solution was stirred at room temperature overnight. The pH of the mixture was adjusted to 2.5 by addition of 6 N hydrochloric acid, and the mixture was extracted with dichloromethane. The organic layer was dried over sodium sulfate, filtered, concentrated, and precipitated into diethyl ether. The product m-$PEG_{10k}$-carboxymethyl acid was collected by filtration and dried under vacuum. Yield: 24 g. NMR ($d_6$-DMSO): 3.21 ppm (s, —$OCH_3$); 3.5 ppm (s, —O—$CH_2CH_2$—O—); 3.99 ppm (s, 2H, —O—$CH_2$—COOH).

$mPEG_{10k}$-carboxymethyl acid (6 g, 0.6 mmol) was then dissolved in anhydrous dichloromethane (30 mL) followed by the addition of 4-aminobutylraldehyde diethylacetal (140 ml, 0.9 mmol), 1-hydroxybenzotriazole (80 mg, 0.6 mmol), and dicyclohexylcarbodiimide (160 mg, 0.78 mmol). The mixture was stirred overnight at room temperature under argon. The reaction mixture was filtered, concentrated, and precipitated with mixture of 2-propanol and diethyl ether (1:1). The $mPEG_{10k}$-butanoacetal product was dried in vacuo overnight. Yield: 5.4 g. NMR ($d_6$-DMSO): 1.07–1.12 ppm (t, 6H, (—O—$CH_2$—$CH_3$)$_2$); 1.46 ppm (m, 4H, —$NHCH_2CH_2CH_2$—CH—); 3.08–3.11 ppm (q, 2H, —$NHCH_2CH_2CH_2$—CH—); 3.21 ppm (s, —$OCH_3$); 3.5 ppm (s, —O—$CH_2CH_2$—O—); 3.85 ppm (s, 2H, —O—$CH_2$—CO—NH—); 4.44 ppm (t, 1H, —$NHCH_2CH_2CH_2$—CH—); 7.67 ppm (—NH—).

$mPEG_{10k}$-butanoacetal (2 g, 0.2 mmol) was then dissolved in 20 mL of 80% $CF_3COOH$ and the solution was stirred at room temperature overnight. The pH of the mixture was adjusted to 6.0 by addition of 1 N NaOH solution, and sodium chloride (10 wt %) was added and then the pH of the solution was adjusted to 7.0 by addition of 1 N NaOH. The mixture was extracted with dichloromethane. The organic layer was dried over sodium sulfate, filtered, concentrated, and precipitated into diethyl ether. The product $mPEG_{10k}$-butanoaldehyde was collected by filtration and dried under vacuum. Yield: 1.7 g. NMR ($d_6$-DMSO): 3.21 ppm (s, —$OCH_3$); 3.5 ppm (s, —O—$CH_2CH_2$—O—); 3.85 ppm (s, 2H, —O—$CH_2$—CO—NH—); 7.67 ppm (—NH—); 9.66 ppm (—CHO—).

EXAMPLE 2

Pegylation of T20 with $PEG_{10K}$-butanoaldehyde

Butanoaldehyde of PEG 10 kDa (from Example 1) was added to 15 mg of T20 (purity 93.7%) in 3.0 ml of buffer (50 mM potassium phosphate pH 6.5) in a molar ratio of 5 moles of reagent per one mole of T20. The T20 polypeptide was deacylated at the α-amino terminus, but protected at the carboxyl terminus by —$NH_2$. To the reaction mixture 10% (V/V) of 0.5 M sodium cyanoborohydride solution in water was added and stirred for 4 hours at room temperature. Pegylated T20 was purified from the reaction mixture using ion exchange chromatography (QA). A linear gradient with increasing salt concentrations from 150 mM to 1 M NaCl in 20 mM Tris, pH 7.5 was used to separate pegylated T20 and unmodified T20.

EXAMPLE 3

Pegylation of T20 with $mPEG_{10k}$-propionaldehyde

A propionaldehyde of PEG 10 kDa, having the following structure is used.

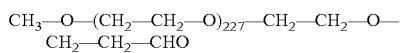

150 mg of mPEG10k-propionaldehyde was added to 15 mg of T20 (purity 93.7%) in 3.0 ml of buffer (50 mM potassium phosphate pH 6.5) in a molar ratio of 5 moles of reagent per one mole of T20. The T1249 polypeptide was deacylated at the α-amino terminus, but protected at the carboxyl terminus by —$NH_2$.

To the reaction mixture 10% (V/V) of 0.5 M sodium cyanoborohydride solution in water was added and stirred for 4 hours at room temperature. Pegylated T20 was purified from the reaction mixture using ion exchange chromatography (QA). The structure of the pegylated T20 polypeptide follows:

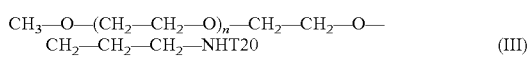

A linear gradient with increasing salt concentrations from 150 mM to 1 M NaCl in 20 mM Tris, pH 7.5 was used to separate pegylated T20 and unmodified T20.

EXAMPLE 4

Inhibitor Concentration for Pegylated T20

Phenotypic susceptibility is usually quantified in terms of IC50 or IC90 a measure of the concentration of drug needed to inhibit 50% or 90%, respectively, of viral growth.

Inhibitor concentration 50 and inhibitor concentration 90 results for the pegylated T20 with $PEG_{10k}$-propionaldehyde (Example 3) and pegylated T20 with mPEG10k-butanoaldehyde (Example 2) has been reproduced in Table 1 below:

TABLE 1

Inhibitor concentration 50 and inhibitor concentration 90 results.

| Pegylated T20 | IC50 (µg/ml) | IC90 (µg/ml) |
|---|---|---|
| Pegylated T20 with mPEG10k-propionaldehyde (Example 3) | 0.261 | 3.074 |
| Pegylated T20 with $PEG_{10K}$-butanoaldehyde (Example 2) | 0.266 | 2.536 |

The IC50 AND IC90 values were determined in accordance with Example 5.

EXAMPLE 5 cMAGI/MAGI Antiviral Assays

These assays score for reduction of infectious virus titer employing the indicator cell lines MAGI (Multinuclear Activation of a Galactosidase Indicator)or the CCR5-expressing derivative cMAGI. The MAGI cell line was derived from parental HeLa cells by introducing genes for CD4 and an HIV-1 LTR-driven b-gal reporter with an amphotropic retrovirus vector (Kimpton J, Emerman M, J Virol 66:2232–9, 1992). The cMAGI cell line was derived from the MAGI cell line by introduction of the CCR5 gene using the amphotropic retroviral vector, PA317 (Chackerian B, Long E M, Luciw P A, Overbaugh J, J Virol 71:3932–9, 1997.). The cMAGI cells support replication of primary NSI (R5) isolates and laboratory adapted X4 viruses, while the MAGI cells support replication of only X4 viruses. Both cell lines exploit the ability of HIV-1 tat to transactivate the expression of a b-galactosidase reporter gene driven by the HIV-LTR. The b-gal reporter has been modified to localize in the nucleus and can be detected with the X-gal substrate as intense nuclear staining within a few days of infection. The number of stained nuclei can thus be interpreted as equal to the number of infectious virions in the challenge inoculum if there is only one round of infection prior to staining.

An inhibitor of infection and cell-cell fusion,e.g., T20 or T1249 (Wild C, Greenwell T, Matthews T, AIDS Res Hum Retroviruses 9:1051–3, 1993), was added 24 hrs post-infection in order to permit a readout that confidently represents a single round of infection. Infected cells were enumerated using a CCD-imager and both primary and laboratory adapted isolates showed a linear relationship between virus input and the number of infected cells visualized by the imager. In the MAGI and cMAGI assays a 50% reduction in infectious titer ($V_n/V_o$=0.5) is significant and provides the primary cutoff value for assessing antiviral activity. A 90% reduction in infectious titer ($V_n/V_o$) is used as an additional cutoff value on assessing antiviral activity.

Each test compound dilution was tested in duplicate against a virus inoculum adjusted to yield approximately 1500–2000 infected cells/well of a 48 well micro titer plate. The test compound was added to the cMAGI or MAGI cells, followed by the virus inocula, and 24 hrs later, an inhibitor of infection and cell-cell fusion (Wild C, Greenwell T, Matthews T, AIDS Res Hum Retroviruses 9:1051–3, 1993) was added to prevent secondary rounds of infection and cell-cell virus spread. The cells were cultured for 2 more days, fixed and stained with the X-gal substrate to detect infected cells. The number of infected cells for each control and test compound dilution were determined with the CCD-imager. IC50 is defined as the dilution of a text compound resulting in a 50% reduction in infectious virus titer. IC90 is defined as the dilution resulting in a 90% reduction in infectious titer.

The invention being thus described, it will be obvious that the same may be varied in many ways. Such variations are not to be regarded as a departure from the spirit and scope of the invention and all such modifications are intended to be included within the scope of the following claims.

What is claimed:

1. A compound of formula (I):

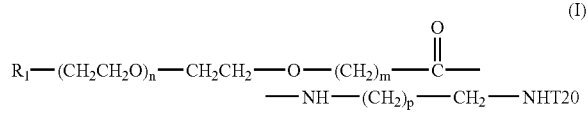

wherein
R₁ is a capping group,
m is from 1 to 17,
n is from 10 to 1,000,
p is from 1 to 3, and
NHT20 is a T20 polypeptide covalently bonded through its terminal α-amino group.

2. A compound according to claim 1, wherein R₁ is selected from the group consisting of halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and

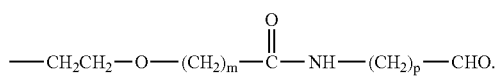

3. A compound according to claim 1, wherein R₁ is

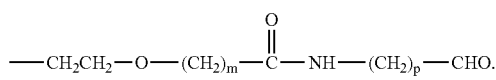

4. A compound according to claim 1, wherein R₁ is selected from the group consisting of hydrogen, hydroxy, lower alkyl, lower alkoxy, lower cycloalkyl, lower alkenyl, aryl, and heteroaryl.

5. A compound according to claim 1, wherein R₁ is selected from the group consisting of methoxy, hydroxy, and benzyloxy.

6. A compound according to claim 5, wherein R₁ is methoxy.

7. A compound according to claim 1, wherein p is 3.

8. A compound according to claim 7, wherein R₁ is selected from the group consisting of methoxy, hydroxy, or benzyloxy.

9. A compound according to claim 7, wherein m is from 1 to 14.

10. A compound according to claim 9, wherein m is from 1 to 7.

11. A compound according to claim 10, wherein m is from 1 to 4.

12. A compound according to claim 7, wherein n is from 20 to 1,000.

13. A compound according to claim 12, wherein n is from 50 to 1,000.

14. A compound according to claim 13, wherein n is from 75 to 1,000.

15. A compound according to claim 1, wherein p is 3, R₁ is methoxy, m is 1, and n is from 100 to 750.

16. A compound according to claim 1, wherein p is 2.

17. A compound according to claim 16, wherein R₁ is selected from the group consisting of methoxy, hydroxy, or benzyloxy.

18. A compound according to claim 16, wherein m is from 1 to 14.

19. A compound according to claim 18, wherein m is from 1 to 7.

20. A compound according to claim 19, wherein m is from 1 to 4.

21. A compound according to claim 16, wherein n is from 20 to 1,000.

22. A compound according to claim 21, wherein n is from 50 to 1,000.

23. A compound according to claim 22, wherein n is from 75 to 1,000.

24. A compound according to claim 1, wherein p is 2, R₁ is methoxy, m is 1, and n is from 100 to 750.

25. A compound according to claim 1, wherein p is 1.

26. A compound according to claim 25, wherein R₁ is selected from the group consisting of methoxy, hydroxy, or benzyloxy.

27. A compound according to claim 25, wherein m is from 1 to 14.

28. A compound according to claim 27, wherein m is from 1 to 7.

29. A compound according to claim 28, wherein m is from 1 to 4.

30. A compound according to claim 25, wherein n is from 20 to 1,000.

31. A compound according to claim 30, wherein n is from 50 to 1,000.

32. A compound according to claim 31, wherein n is from 75 to 1,000.

33. A compound according to claim 1, wherein p is 1, R₁ is methoxy, m is 1, and n is from 100 to 750.

34. A compound of formula:

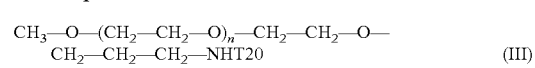

wherein n is from 10 to 1,000 and NHT20 is a T20 polypeptide covalently bonded through its terminal α-amino group.

35. A compound according to claim 34, wherein n is approximately 225.

36. A pharmaceutical composition comprising, in admixture with a pharmaceutically acceptable excipient, a compound of formula:

$$R_1-(CH_2CH_2O)_n-CH_2CH_2-O-(CH_2)_m-\overset{O}{\underset{\|}{C}}-NH-(CH_2)_p-CH_2-NHT20 \quad (I)$$

wherein
$R_1$ is a capping group,
m is from 1 to 17,
n is from 10 to 1,000,
p is from 1 to 3, and
NHT20 is a T20 polypeptide covalently bonded through its terminal α-amino group.

37. A pharmaceutical composition according to claim 36, wherein $R_1$ is selected from the group consisting of halogen, epoxide, maleimide, orthopyridyl disulfide, tosylate, isocyanate, hydrazine hydrate, cyanuric halide, N-succinimidyloxy, sulfo-N-succinimidyloxy, 1-benzotriazolyloxy, 1-imidazolyloxy, p-nitrophenyloxy, and $$-CH_2CH_2-O-(CH_2)_m-\overset{O}{\underset{\|}{C}}-NH-(CH_2)_p-CHO.$$

38. A pharmaceutical composition according to claim 36, wherein $R_1$ is $$-CH_2CH_2-O-(CH_2)_m-\overset{O}{\underset{\|}{C}}-NH-(CH_2)_p-CHO.$$

39. A pharmaceutical composition according to claim 36, wherein $R_1$ is selected from the group consisting of hydrogen, hydroxy, lower alkyl, lower alkoxy, lower cycloalkyl, lower alkenyl, aryl, and heteroaryl.

40. A pharmaceutical composition according to claim 36, wherein $R_1$ is selected from the group consisting of methoxy, hydroxy, and benzyloxy.

41. A pharmaceutical composition according to claim 36, wherein $R_1$ is methoxy.

42. A pharmaceutical composition according to claim 36, wherein p is 3.

43. A pharmaceutical composition according to claim 42, wherein $R_1$ is selected from the group consisting of methoxy, hydroxy, or benzyloxy.

44. A pharmaceutical composition according to claim 43, wherein m is from 1 to 14.

45. A pharmaceutical composition according to claim 44, wherein m is from 1 to 7.

46. A pharmaceutical composition according to claim 45, wherein m is from 1 to 4.

47. A pharmaceutical composition according to claim 42, wherein n is from 20 to 1,000.

48. A pharmaceutical composition according to claim 47, wherein n is from 50 to 1,000.

49. A pharmaceutical composition according to claim 48, wherein n is from 75 to 1,000.

50. A pharmaceutical composition according to claim 36, wherein p is 3, $R_1$ is methoxy, m is 1, and n is from 100 to 750.

51. A pharmaceutical composition according to claim 36, wherein p is 2.

52. A pharmaceutical composition according to claim 51, wherein $R_1$ is selected from the group consisting of methoxy, hydroxy, or benzyloxy.

53. A pharmaceutical composition according to claim 51, wherein m is from 1 to 14.

54. A pharmaceutical composition according to claim 53, wherein m is from 1 to 7.

55. A pharmaceutical composition according to claim 54, wherein m is from 1 to 4.

56. A pharmaceutical composition according to claim 51, wherein n is from 20 to 1,000.

57. A pharmaceutical composition according to claim 56, wherein n is from 50 to 1,000.

58. A pharmaceutical composition according to claim 57, wherein n is from 75 to 1,000.

59. A pharmaceutical composition according to claim 36, wherein p is 2, $R_1$ is methoxy, m is 1, and n is from 100 to 750.

60. A pharmaceutical composition according to claim 36, wherein p is 1.

61. A pharmaceutical composition according to claim 60, wherein $R_1$ is selected from the group consisting of methoxy, hydroxy, or benzyloxy.

62. A pharmaceutical composition according to claim 60, wherein m is from 1 to 14.

63. A pharmaceutical composition according to claim 62, wherein m is from 1 to 7.

64. A pharmaceutical composition according to claim 63, wherein m is from 1 to 4.

65. A pharmaceutical composition according to claim 60, wherein n is from 20 to 1,000.

66. A pharmaceutical composition according to claim 65, wherein n is from 50 to 1,000.

67. A pharmaceutical composition according to claim 66, wherein n is from 75 to 1,000.

68. A pharmaceutical composition according to claim 36, wherein p is 1, $R_1$ is methoxy, m is 1, and n is from 100 to 750.

69. A pharmaceutical composition according to claim 36 in the form of a lypholized powder.

70. A pharmaceutical composition according to claim 36 in the form of an injectable solution or suspension.

71. A pharmaceutical composition according to claim 50 in the form of a lypholized powder.

72. A pharmaceutical composition according to claim 50 in the form of an injectable solution or suspension.

73. A pharmaceutical composition according to claim 36 in unit dosage form.

74. A pharmaceutical composition according to claim 73, wherein the unit dosage form is an injectable solution or suspension.

75. A pharmaceutical composition according to claim 73, wherein the unit dosage form is a transdermal delivery device.

76. A pharmaceutical composition according to claim 50 in unit dosage form.

77. A pharmaceutical composition according to claim 76, wherein the unit dosage form is an injectable solution or suspension.

78. A pharmaceutical composition according to claim 76, wherein the unit dosage form is a transdermal delivery device.

79. A pharmaceutical composition comprising, in admixture with a pharmaceutically acceptable excipient, a compound of formula:

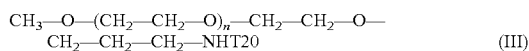
(III)

wherein n is from 10 to 1,000 and NHT20 is a T20 polypeptide covalently bonded through its terminal α-amino group.

80. A pharmaceutical composition according to claim 79, wherein n is approximately 225.

81. A method of inhibiting HIV infection comprising administering a pharmaceutical composition comprising, in admixture with a pharmaceutically acceptable excipient, a compound of formula:

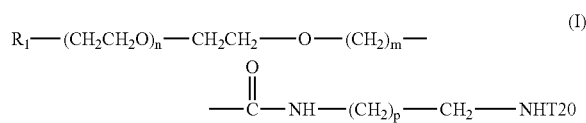
(I)

wherein
R$_1$ is a capping group,
m is from 1 to 17,
n is from 10 to 1,000,
p is from 1 to 3, and
NHT20 is a T20 polypeptide covalently bonded through its terminal α-amino group.

82. A method according to claim 81, wherein the pharmaceutical composition is administered in an amount of from about 50 mg to about 200 mg per day.

83. A method according to claim 81, wherein the pharmaceutical composition is administered in an amount of from about 300 mg to about 1500 mg per week in a single dose.

84. A method according to claim 83, wherein the pharmaceutical composition is administered in an amount of from about 400 mg to about 1000 mg per week in a single dose.

85. A method according to claim 84, wherein the pharmaceutical composition is administered in an amount of from about 500 mg to about 800 mg per week in a single dose.

86. A method of inhibiting HIV infection comprising administering a pharmaceutical composition comprising, in admixture with a pharmaceutically acceptable excipient, a compound of formula:

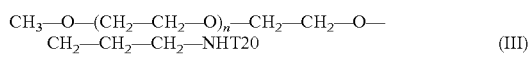
(III)

wherein n is from 10 to 1,000 and NHT20 is a T20 polypeptide covalently bonded through its terminal α-amino group.

87. A method according to claim 86, wherein n is approximately 130.

88. A compound of formula:

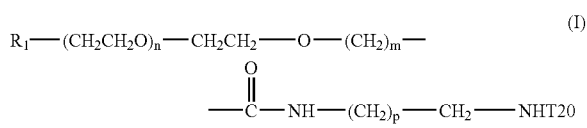
(I)

wherein
R$_1$ is methoxy,
m is 1,
n is from 100 to 750,
p is 3, and
NHT20 is a T20 polypeptide covalently bonded through its terminal α-amino group.

89. A pharmaceutical composition comprising, in admixture with a pharmaceutically acceptable excipient, a compound of formula:

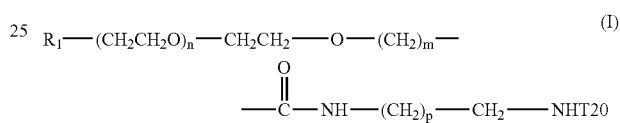
(I)

wherein
R$_1$ is methoxy,
m is 1,
n is from 100 to 750,
p is 3, and
NHT20 is a T20 polypeptide covalently bonded through its terminal α-amino group.

90. A method of inhibiting HIV infection comprising administering a pharmaceutical composition comprising, in admixture with a pharmaceutically acceptable excipient, a compound of formula:

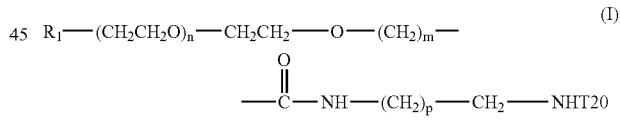
(I)

wherein
R$_1$ is methoxy,
m is 1,
n is from 100 to 750,
p is 3, and
NHT20 is a T20 polypeptide covalently bonded through its terminal α-amino group.

91. A method for attaching a polyethylene glycol molecule to a T20 polypeptide comprising reacting a T20 polypeptide with a polyethylene glycol aldehyde of formula:

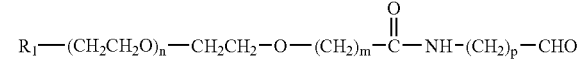

wherein
R$_1$ is a capping group,
m is from 1 to 17, n is from 10 to 1,000, and p is from 1 to 3;

to produce a compound of formula:

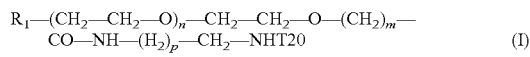

(I)

wherein the polyethylene glycol aldehyde molecule is bonded to the N-terminal amino group of the T20 polypeptide.

92. A method according to claim 91 wherein the T20 polypeptide is reacted with the polyethylene glycol molecule at a pH sufficiently acidic to selectively activate the α-amino group at the amino terminus of the polypeptide.

93. A method according to claim 91 wherein the pH is from about 5.5 to about 7.4.

94. A method according to claim 93 wherein the pH is about 6.5.

95. A method according to claim 91 further comprising isolating the pegylated T20 polypeptide.

* * * * *